(12) United States Patent
Hu

(10) Patent No.: US 7,256,053 B2
(45) Date of Patent: Aug. 14, 2007

(54) DIAGNOSTIC DEVICE FOR ANALYTE DETECTION

(75) Inventor: Wei Hu, Toronto (CA)

(73) Assignee: Nanogen, Inc., San Diego, CA (US)

( * ) Notice: Subject to any disclaimer, the term of this patent is extended or adjusted under 35 U.S.C. 154(b) by 530 days.

(21) Appl. No.: 10/279,566

(22) Filed: Oct. 24, 2002

(65) Prior Publication Data

US 2004/0082077 A1    Apr. 29, 2004

(51) Int. Cl.
*G01N 33/53* (2006.01)
(52) U.S. Cl. .................. 436/514; 436/518; 422/56; 422/57; 422/58
(58) Field of Classification Search ............ 422/56–58; 436/514, 518
See application file for complete search history.

(56) References Cited

U.S. PATENT DOCUMENTS

| | | | |
|---|---|---|---|
| 5,354,692 A | 10/1994 | Yang et al. | |
| 5,559,041 A | 9/1996 | Kang et al. | |
| 5,712,172 A | 1/1998 | Huang et al. | |
| 5,879,951 A | 3/1999 | Sy | |
| 5,885,526 A | 3/1999 | Chu | |
| 6,171,870 B1 | 1/2001 | Freitag | |
| 6,214,629 B1 | 4/2001 | Freitag et al. | |
| 6,306,642 B1 | 10/2001 | Nelson et al. | |
| 6,410,341 B1 | 6/2002 | Freitag et al. | |
| 6,656,745 B1 * | 12/2003 | Cole | 436/514 |
| 2002/0086436 A1 * | 7/2002 | Buechler | 436/164 |
| 2003/0103869 A1 * | 6/2003 | Hardman et al. | 422/58 |

FOREIGN PATENT DOCUMENTS

| | | |
|---|---|---|
| EP | 0 888 547 | 12/2003 |
| WO | WO 88/08534 | * 11/1988 |
| WO | WO 00/08466 | 2/2000 |
| WO | WO 01/25789 | 4/2001 |
| WO | WO 01/27627 | 4/2001 |

* cited by examiner

*Primary Examiner*—Bao-Thuy L. Nguyen
(74) *Attorney, Agent, or Firm*—Morgan Lewis & Bockius LLP; Jeffry S. Mann; Ada O. Wong

(57) ABSTRACT

The present invention provides a hand-held device of the type useful to perform an in vitro immunodiagnostic assay for an analyte of interest. In embodiments of the invention, the device incorporates a carrier for conducting the assay which comprises an array of pads including a sample pad, a narrow detection pad for detecting analyte, and a bridging pad coupled in flow communication therebetween. The device is provided with a housing adapted to deliver sample onto the carrier as a linear band having a width greater than the detection pad. In combination, these features yield a device that retains the sensitivity required for diagnostic accuracy, yet is improved in terms of cost and ease of manufacture.

16 Claims, 7 Drawing Sheets

Sample flow direction →

Signal ↓

Signal ↓

DIAGNOSTIC DEVICE FOR ANALYTE DETECTION

FIELD OF THE INVENTION

This invention relates to the detection of analytes including those that are relevant in medical diagnosis. More particularly, the invention relates to devices that typically are hand-held and allow for the detection of analytes in specimens such as body fluids, environmental samples and the like.

BACKGROUND OF THE INVENTION

A wide variety of devices are now available for detecting analytes present in body fluids, such as whole blood, plasma, serum and urine, to aid in medical diagnosis. The simplest form of such a device performs the in vitro diagnostic test on the surface of a dry porous carrier, such as a sheet or strip of nitrocellulose membrane, which is usually contained within a housing that defines a sample application site and a detection site for viewing the assay result. In the so-called "spot test", sample is applied as a drop to a carrier having immobilized thereon a reagent capable of binding to the analyte targeted for detection. After washing the carrier, the presence of bound analyte is revealed by incubation with an analyte-specific labeling agent. An alternative one-step approach, the so-called "lateral flow" format, similarly makes use of a reagent that is immobilized on the carrier. In this format, sample is applied to one end of a nitrocellulose strip, and flows by capillary action toward reagent immobilized at the other end. As the sample migrates along the strip, additional mobile reagents become entrained in the sample stream so that, typically, a detectable reagent "sandwich" is developed at the other end, consisting of the immobilized reagent, the analyte of interest, and an analyte-binding detector reagent that is labeled to reveal the analyte's presence.

Diagnostic devices of this type are intended to be disposable after a single use, and must therefore be designed for inexpensive production. Importantly, however, the engineering required to perform the test in a rapid and reproducible fashion, with maximum sensitivity and specificity and with minimum sample volume, is highly demanding. The art is therefore continuously refining the design of such devices in order to improve their price and practicality.

One device, which incorporates numerous improvements over those currently marketed, is described in WO00/08466 published Feb. 17, 2000 in the name of the present assignee. Described therein is a diagnostic device that, like many others, incorporates both a dry porous carrier in the form of a nitrocellulose sheet, and a housing for that carrier that incorporates both a sample inlet and a window for viewing the assay result. The sample inlet of the device is particularly unique, in providing a U-shaped channel from which sample can be deposited across a wide sample deposition zone for capillary flow into a narrowed detection channel in which the analyte is captured for detection. By channeling the flow of sample confocally through the mobile reagents located upstream in the deposition zone, the device concentrates reagents and analyte and retards red blood cell migration, and thereby enhances the sensitivity of the assay for a given volume of sample.

That device utilizes a carrier that most desirably is a uniplanar, single sheet of nitrocellulose, and uses both the housing and repellant border material to drive sample flow from the sample zone to the relatively narrow detection channel. In other devices, a multiplanar construction is incorporated in which the various pads, formed of the carrier material, are coupled in flow communication. In this arrangement, each pad can be used for a different purpose. For instance, and as shown in co-assigned U.S. Pat. No. 5,658,801, each one of a plurality of pads can be impregnated with a different one of the various reagents required to detect a given analyte by the lateral flow method. These pads can then be "stacked" one above the other and in flow communication with a base carrier. Reagents deposited in the pads are picked up by sample that has been applied to the top pad, and any complexes formed with the analyte then are captured by reagent immobilized downstream on the base carrier, where a reading can be taken.

In an alternative multi-pad design, described for instance in U.S. Pat. No. 5,559,041, a sample pad optionally impregnated with reagent is positioned in flow communication with a detection pad bearing immobilized reagent. One or more intervening pads are also incorporated, to function as a filter for particulates contained in the sample.

Despite these advances in diagnostic devices, there remains a need to improve the ease with which they can be used and manufactured, without sacrificing their reliability.

It is an object of the present invention to provide an improved device for detection of analytes in a liquid sample.

SUMMARY OF THE INVENTION

The present invention provides a device of the type useful to perform an in vitro immunodiagnostic assay for an analyte of interest. The present device can be used particularly, but not exclusively, to detect the presence of cardiac analytes in a sample of whole blood, serum or plasma, including for instance troponin I, C and/or T, myoglobin, myosin light chain, creatine kinase M and/or B, and the like. The device is adapted to be hand-held, and to provide rapid and reliable results using sample volumes as small as the blood volume generated from a single finger prick. In addition to its versatility and convenience, the present device is engineered and designed for production at low cost and with minimum labour and waste, relative to devices with similar high performance and diagnostic accuracy.

The present device utilizes a carrier that is adapted for highly efficient sample flow, which not only maximizes use of sample volume but also maximizes analyte flow across the analyte capture line. In one embodiment of the present device, this is achieved using a carrier formed of an array of pads, including a sample pad for receiving sample, and at least one detection pad which defines a detection channel having a width that is narrower than the sample pad. In a preferred embodiment, the detection channel comprises both a detection pad and a bridging pad that is coupled in flow communication between the sample pad and the detection pad. In a preferred embodiment, the bridging pad has a lower surface that is in contact with the upper surfaces of the sample pad and the detection pad. By this arrangement, there is provided an interface that functions to filter certain particulates from the sample migrating across the carrier pad array. In a further preferred embodiment, the bridging pad and the detection pad are coupled using an upper barrier layer that is impervious to liquid. By this arrangement, capillary flow is enhanced for all sample migrating into the detection channel, thereby increasing and concentrating the flow of sample, and analyte, across the detection pad.

By providing a carrier that is modular in design and comprises individual pads, the present device can be produced with far less waste of carrier material than a single carrier sheet that performs similarly, to channel sample into a narrow detection channel. Moreover, the rate and volume of sample flow across the detection pad is increased, relative to a single sheet design, by using the overlapping pad arrangement and barrier layer by which the various pads are coupled in flow communication.

Also in the present device, there are provided certain key features that simplify manufacturing and handling of the device during use and transportation. The present device comprises a housing and a carrier material having a surface suitable for conducting the assay, which in one embodiment is constituted by the pad array just described. In the present device, the housing is provided with a sample inlet that communicates with the carrier by way of a sample deposition channel. In the present device, the sample deposition channel is adapted to deposit sample as a generally linear band having its longer axis generally transverse to the path of sample flow on the carrier. Desirably, the width of the sample band deposited from the deposition channel is greater than the width of the detection channel through which the deposited sample migrates. As distinct from sample deposition channels that are U-shaped, the present linear deposition channel offers greater ease of manufacture. Moreover, it has been found that the U-shaped design, intended to channel sample for confocal flow toward a narrow detection channel is unnecessary; sample deposited from a linear band that is perpendicular to sample flow and wider than the downstream detection channel, as in the present invention, has been found to migrate naturally toward and into the detection channel without significant loss of sample to regions of flow stagnation. Moreover, by this arrangement, reagent-bound analyte becomes concentrated at the entry to the detection channel, and thus migrates across the detection pad in concentrated form to enhance assay sensitivity.

These and other aspects and embodiments of the present device are now described with reference to the accompanying drawings in which:

DETAILED DESCRIPTION

Description of Preferred Embodiments of the Invention

Figure 1:
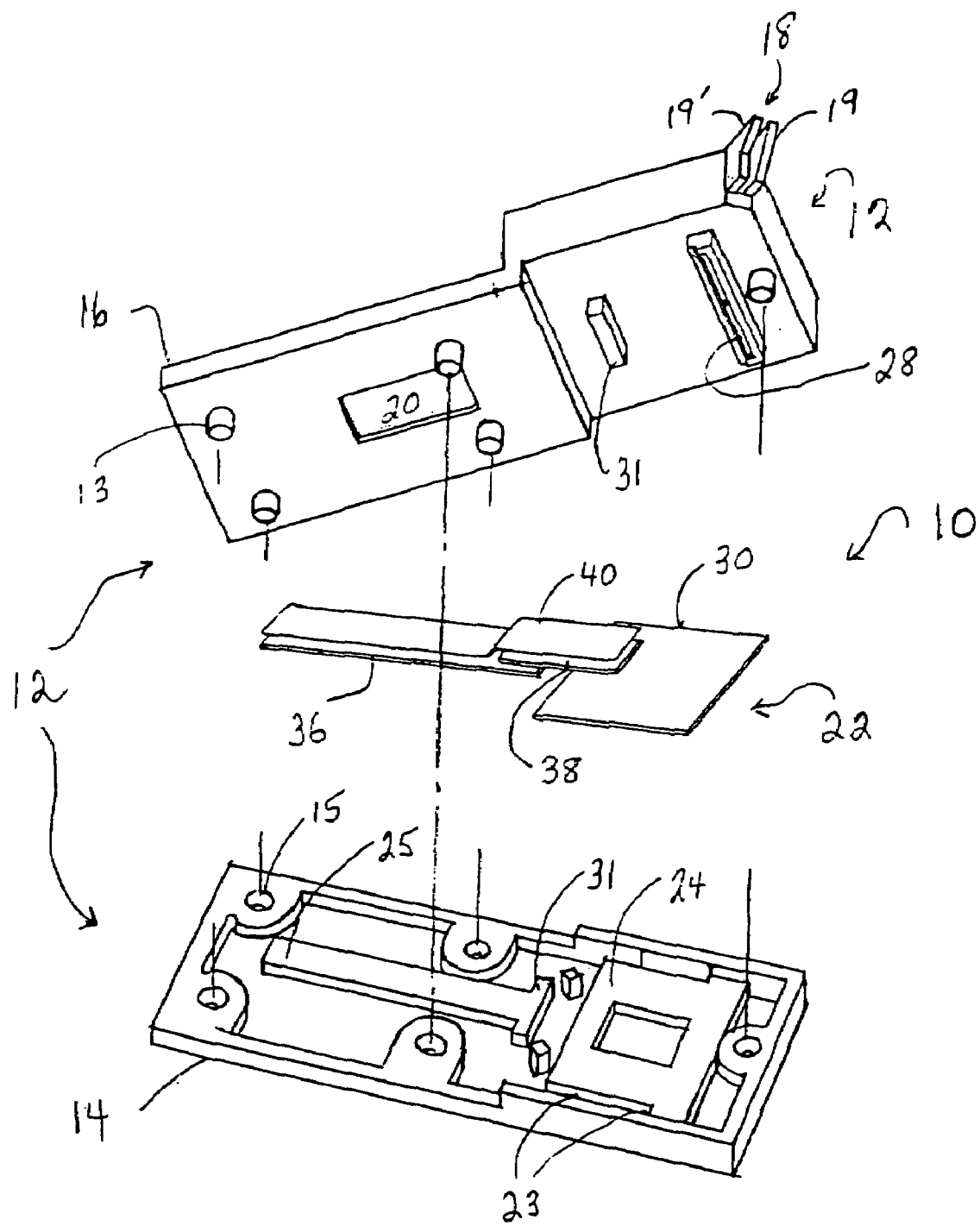
FIG. 1 is a perspective, exploded view of a device of the present invention showing the components in alignment.

In an embodiment of the present invention, a device 10 shown in FIG. 1 comprises a housing 12 formed of a base member 14 and an upper member 16 that are mateable, by friction fit, between pins 13 and corresponding recesses 15 formed in base 14. Upper member 16 is provided with a sample receiving port 18 for receiving sample to be assayed, and a window 20 for viewing the assay result. The housing contains a suitable porous carrier 22, having a surface for conducting sample flow between the sample deposition site and the analyte detection site situated within the window. The housing, and the device generally, are of a size convenient for holding the device in one hand during operation of the test. In the embodiment depicted in FIGS. 1 and 3-6A, the actual device is about one third the size shown.

The housing accommodates carrier 22 between base member 14 and upper member 16. In a preferred embodiment, the carrier 22 has the features illustrated in FIG. 2 to which reference is now made. It will be seen that carrier 22 is comprised of an array of pads coupled in flow communication. The array comprises a sample pad 30 for receiving sample. The pad array further defines a detection channel 34 having a width that is reduced relative to the sample pad. In the illustrated embodiment, the detection channel 34 is comprised of a detection pad 36 and a bridging pad 38. Alternatively, the detection channel can comprise a single detection pad having dimensions comparable to the combined detection and bridging pads. To couple a single detection pad to the sample pad, any backing material on the detection pad can be removed at least at the interface thereof with the sample pad, to foster sample flow from the sample pad into the detection pad defining the detection zone.

The pads within the array carry reagents 32 suitable for detecting the analyte of interest. To perform the typical lateral flow immunoassay, for instance, analyte-binding reagents, also referred to as detector reagents, are deposited on the sample pad 30 downstream from the site 35 at which sample is first applied to the carrier. These analyte-binding reagents are deposited on the carrier as mobile reagents that become entrained in the sample flow for movement with the analyte. These reagents also are typically coupled to a label that can be detected either visually or with suitable instrumentation. Examples of suitable analyte-binding reagents are antibodies bearing such labels as gold sol, enzyme, fluorophore, or lumiphore. Analyte present in the sample stream thus becomes bound to the labeled detector reagent to form analyte-reagent complexes. The complexes migrate into the detection zone 34, where they encounter an analyte-binding capture reagent 39 immobilized on the carrier within view from the window 20. The accumulation of label at the capture line thus reports a positive assay result, confirming that the targeted analyte is present in the sample under investigation.

Figure 2A:
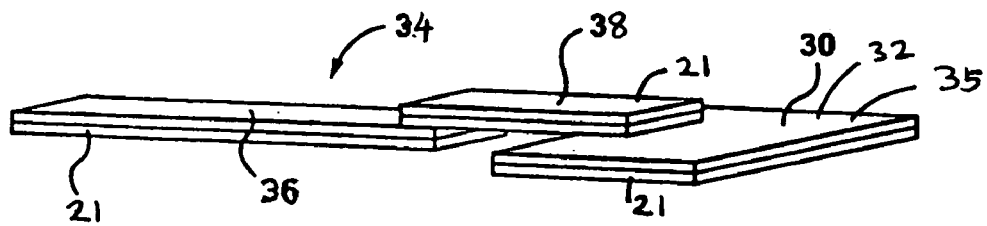
FIG. 2 illustrates the pad arrangement in the device of FIG. 1, in perspective view (panel A), in top view (panel B); in side elevation (panel C); and with a wicking pad in place (panel D).
Figure 2B:
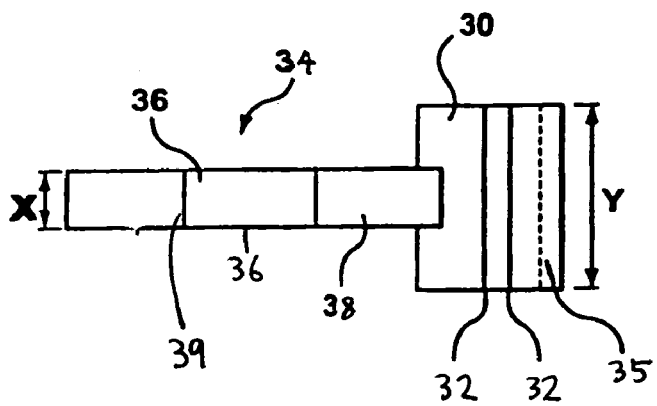
Figure 2C:
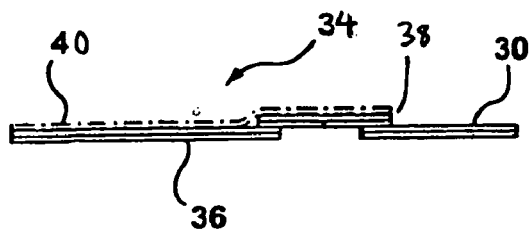
Figure 7A:
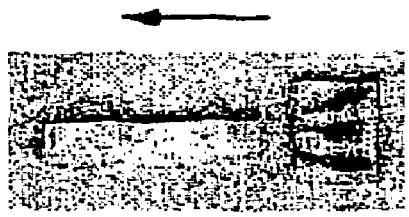
FIG. 7 illustrates results obtained using the device of FIG. 1.

As noted in FIG. 2B, one or more different mobile detector reagents can be deposited as individual bands spanning the width of the sample pad. In the alternative and as shown in FIG. 7A, these detector reagents can be deposited as reagent blots.

There are numerous adaptations of this immunoassay format, including indirect formats and competitive binding formats. It will be appreciated that the particular format chosen for performing the assay is not critical to the present invention, and that any of a variety of formats can be adopted with the present device.

It will further be appreciated that the immobilized capture reagent can be deposited in the shape of any desired indicia, and is illustrated as a straight line. To control for false negative results, the detection pad can further comprise a control line, bearing an immobilized reagent that is non-specific for analyte, but indicates that sample has migrated successfully past the analyte capture line. A binding partner specific for a mobile detector reagent deposited in the sample pad can serve this purpose.

Each pad within the array constituting carrier 22 can be formed of the same carrier material, but this is not essential.

Different carriers and carrier compositions can be used. For instance, the pads can be formed of glass fibers, of nitrocellulose, or of any suitable polymeric material on which liquid sample can flow desirably by capillary action. The carrier further can be made of material suitable for filtering sample as it migrates, or for allowing sample particulates to separate chromatographically as sample migrates therealong. This is of particular benefit when the applied sample is blood. In this case, the structure of the carrier material preferably functions to separate the blood components chromatographically, causing the formation of a plasma front advancing ahead of red cells and other particulate material.

In the embodiment illustrated in FIG. 2, the pads are each formed of nitrocellulose having an average pore size in the 1-10 micron range, e.g., of about 3 microns or about 5 microns. The pads are cut from a larger sheet of nitrocellulose having a backing material 21 that is water-impermeable, to prevent sample leakage, and provides some rigidity to the otherwise supple nitrocellulose material. A suitable such material is polyester film. The pads illustrated in FIG. 2 thus have a backing material, and present only one surface, or face, on which the assay can be conducted. As noted in the Figure, the sample conducting faces of the sample pad and the detection pad are bridged between and in contact with the sample conducting face of the bridging pad. The pads overlap at their edges to establish sample flow communication along the length of the carrier 22. By placing the bridging pad above the sample pad, there is provided a capillary "lift" that assists with filtration of the sample and in the case of a blood sample, further accentuates the chromatographic separation of the sample into a leading plasma front and trailing red blood cells.

Figure 2D:
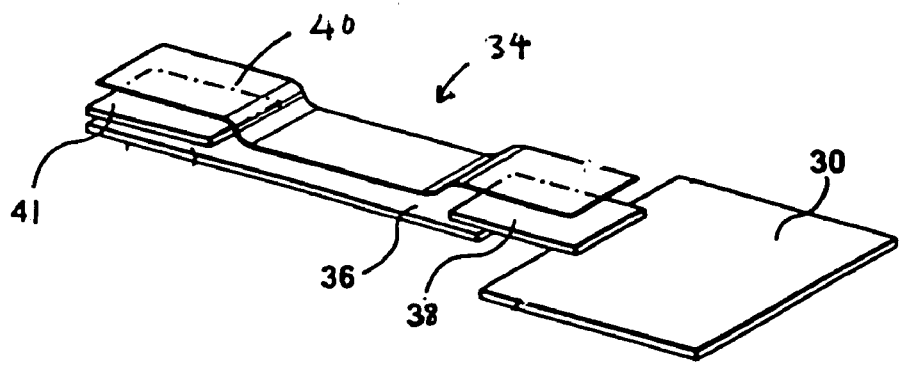
Figure 3:
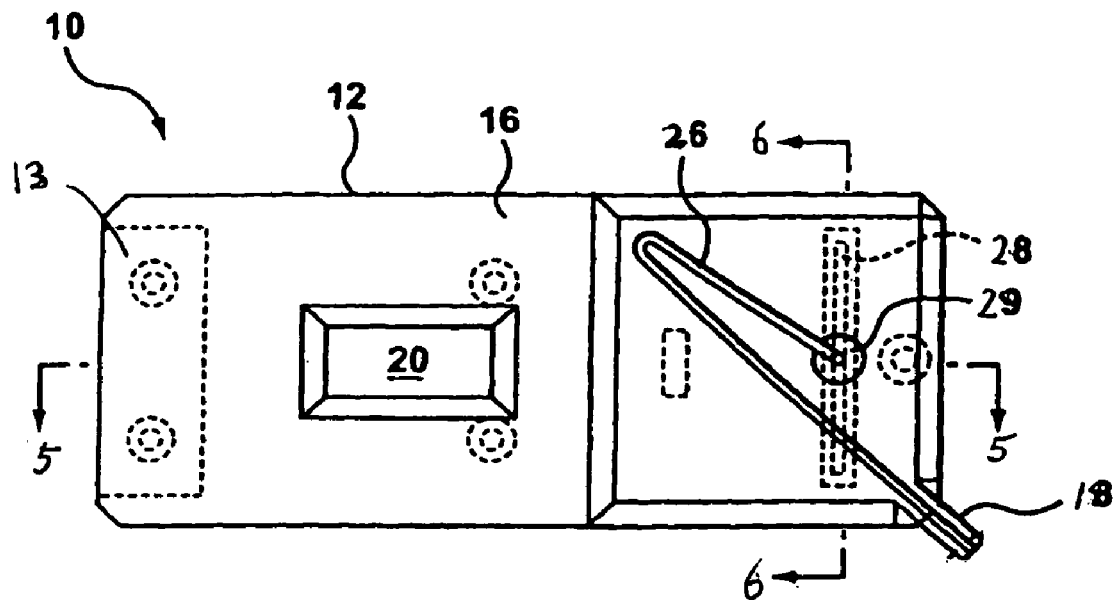
FIG. 3 is a top view of the device of FIG. 1.
Figure 4:
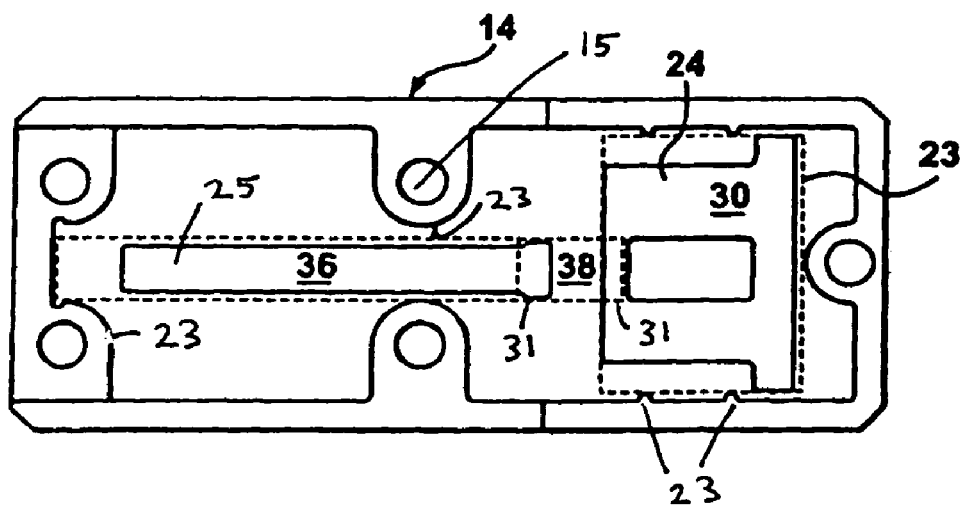
FIG. 4 is a top view of the base member of the housing.

Carrier 22 has a surface area and volume sufficient to accommodate the sample volume required for a given assay. In addition, the zone within detection pad 36 that is downstream of the detection reagents 32 is provided with a surface area sufficient to draw sufficient sample across the capture line to detect the analyte before the carrier is completely wetted by the sample, at which point, further sample migration is inhibited. This can be achieved simply by extending the length of detection pad 36, to provide for sufficient sample draw. Alternatively, and as shown in FIG. 2D, the detection pad can be provided at its distal end with a wicking pad 41 that is positioned in flow communication with the detection pad. The wicking pad can reduce the length of the detection pad, and the overall device, by substituting for an elongated detection pad.

Flow communication between each of the pads in the array can be maintained by "pinching" the pads at their overlapping interfaces using structure provided by the housing, as will be described in greater detail below. Alternatively, or in addition, and according to one embodiment of the present invention, flow communication between the bridging pad and detector pad, and any wicking pad present therewith, can be maintained using a layer of wettable and adhesive barrier material. As illustrated in FIG. 2, the layer of barrier material 40 is applied along substantially the entire length of the detection zone and bridging pad. This ensures that these pads remain in flow communication. In addition, and importantly, it has been found that the layer of barrier material has the effect of enhancing the flow of sample thereunder, and thus has the advantage of effectively drawing sample into the detection channel from the sample pad. It will be appreciated that the layer of barrier material should be either translucent or transparent, so that it does not mask the assay result from being viewed through window 20. Any transparent or translucent barrier material that functions like adhesive tape, such as Scotch® tape, can be used for this purpose. This barrier layer also prevents accidental smearing or damage or other exposure to the carrier exposed at the device viewing window.

It will be noted that the sample pad has a width that is greater than the detection channel coupled to it. This is an important feature of the present carrier system. By this design, sample deposited across the sample pad has been found to migrate in the direction of the detection channel, with very little if any sample stagnation seen in the "shoulder" of the sample pad. In fact, any slowing of sample flow at these "shoulders" provides the benefit that the sample becomes enriched for analyte/label complexes which then can flow in concentrated form into the detection channel, thus enhancing assay sensitivity.

The preferred system for depositing sample onto the carrier 22 is now described in greater detail.

As shown in FIG. 1, the carrier 22, bearing mobile detection reagents on the sample pad and immobilized capture reagents on the detection pad, is received between base member 14 and upper member 16, so that the capture reagent line and any control reagent line are positioned for viewing at window 20. The carrier 22 is registered within the housing by projections 23 formed in base member 14, which abut the periphery of the carrier, to avoid continuous lines of contact with the housing. [FIG. 4]. Also provided in base member 14 are raised platforms or stages 24 and 25, which support the sample pad 30 and detection channel 34, respectively. Also provided directly under the bridging pad at its interfaces with the sample pad and the detection pad are supporting webs, 31.

Figure 5:
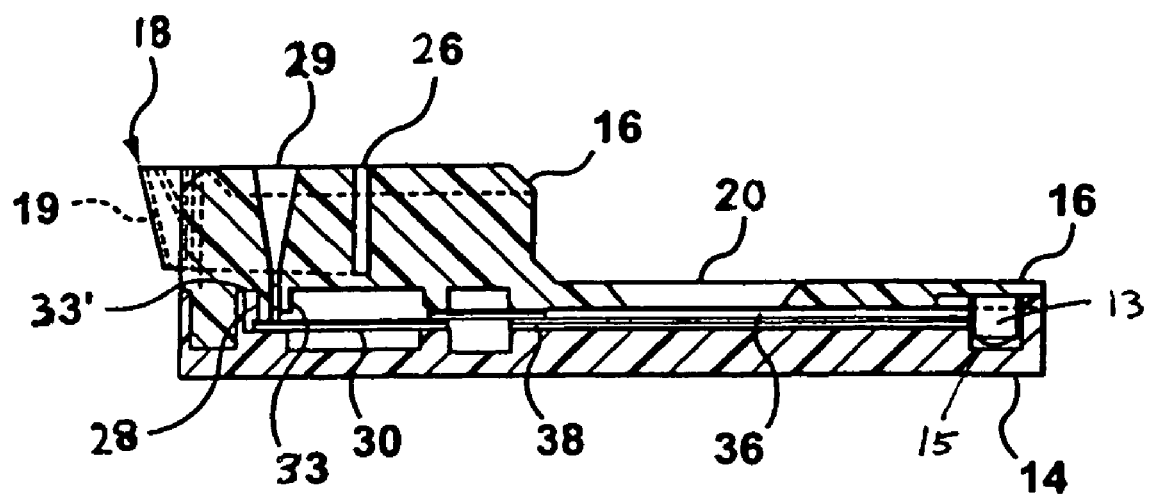
FIG. 5 is a side view along lines 5-5 of FIG. 3.
Figure 6A:
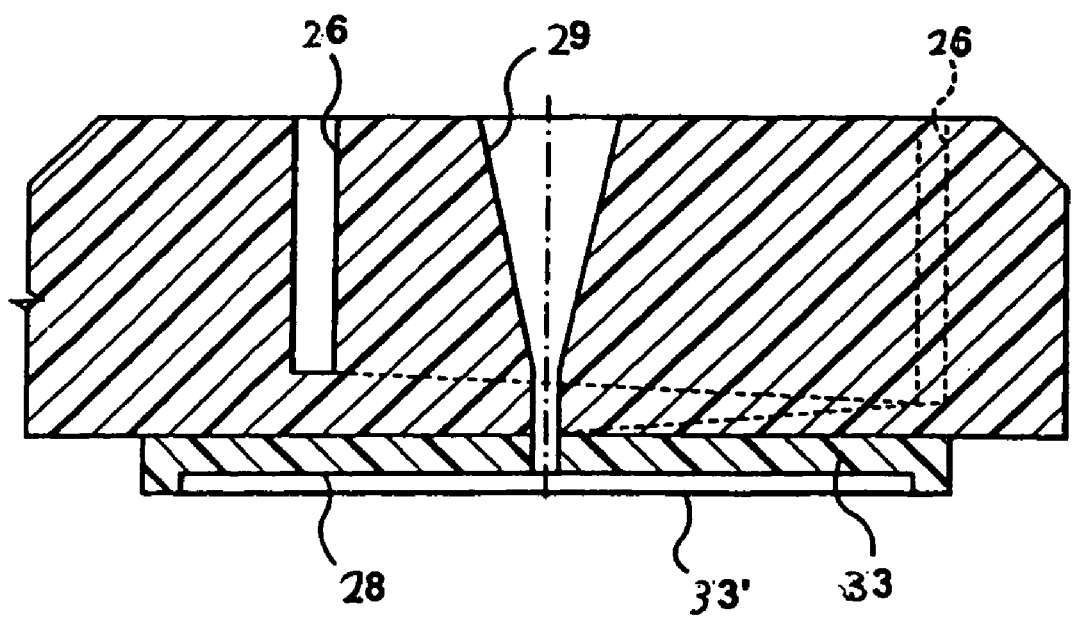
FIG. 6 shows the sample delivery channel in side view along lines 6-6 of FIG. 3 (panel A), and in magnified perspective view from above (panel B) and from below (panel C)
Figure 6B:
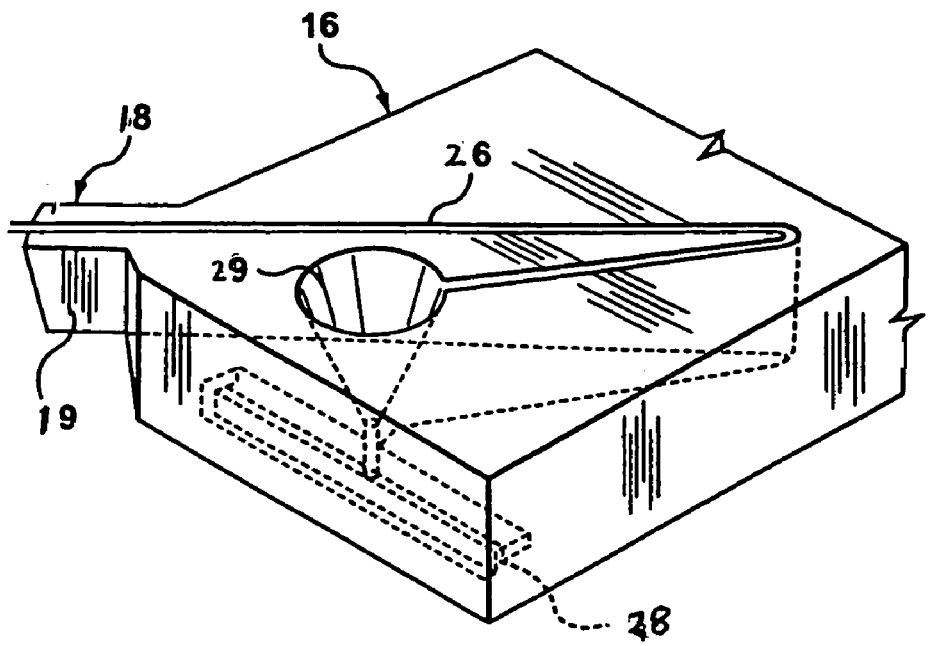
Figure 6C:
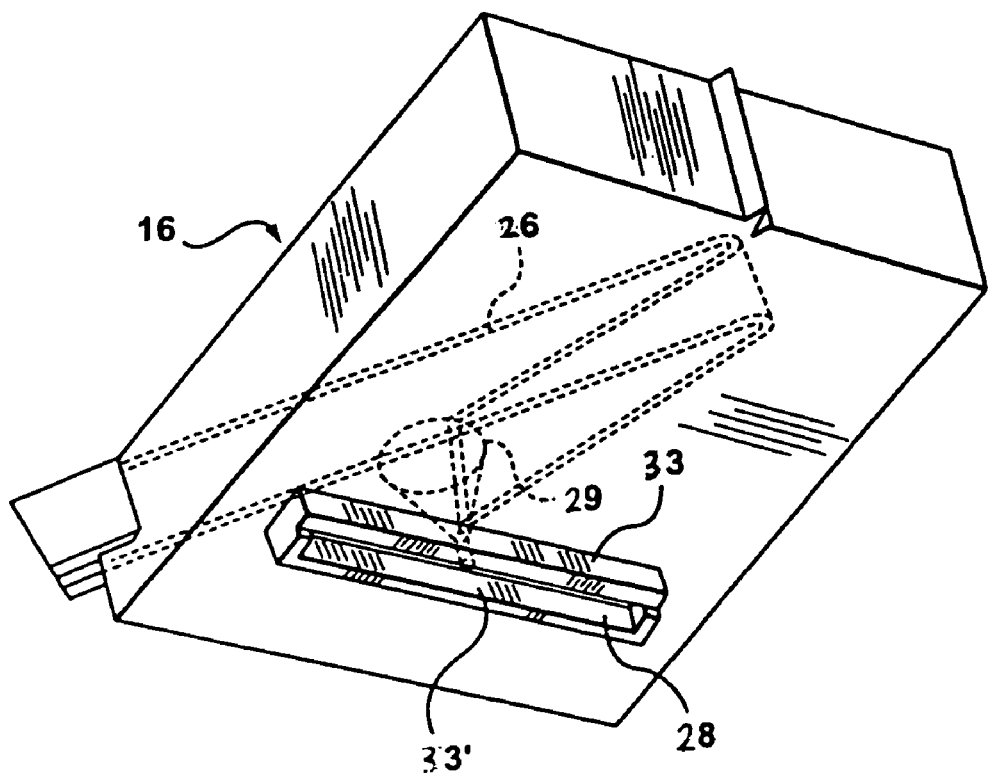

As shown in FIGS. 1, 5 and 6, upper member 16 of the present device has a sample receiving port 18 that communicates with the carrier 22 via a sample deposition means, which comprises a conduit 26 formed within housing upper member 16. Conduit 26 feeds into sample reservoir 29 which communicates with and feeds into sample deposition channel 28, from which sample is ultimately deposited onto carrier 22.

An embodiment of the sample delivery system is shown in greater detail in FIG. 5 and FIG. 6. In the illustrated design, delivery of sample onto the carrier is achieved using a system that drives sample flow by exploiting a combination of surface tension minimization, capillary action, and gravity. More particularly, conduit 26 extends externally to sample receiving port 18 which is defined by first and second flanges, 19 and 19'. As shown in FIG. 1, one of the two flanges is notched to maximize port surface area and thus encourage liquid sample to minimize surface tension by moving into conduit 26. Conduit 26 is formed as a trench within the upper member 16, having a bottom, parallel side walls and a top that is open to the air. The bottom of conduit 26 is shaped to provide increasing depth along the length thereof (revealed in FIG. 6A). Thus, when the device is placed on a horizontal surface, there is a gravitational tendency for sample to flow away from the sample receiving port and into the sample deposition channel. In addition, conduit 26 is reticulated, so that when device 10 is held by the user in a vertical orientation, as would be desirable when applying a sample to be tested, there is a further tendency for sample to move by gravity toward the sample reservoir 29. This is achieved by forming the conduit 26 as a trough that is descending, when the device is held in the vertical position. The conduit 26 desirably has a volume sufficient to hold sample sufficient for performance of a given test. It will be appreciated that this volume can be adjusted by increasing the length of the conduit. As shown in the Figures, this is achieved by reticulating the conduit, in the shape of a hairpin as shown. Any other design, linear or curved, could be adopted to this end. In addition, it will be appreciated that the upper member 16 can include a protective layer of material, such as a fixed or removable adhesive tape (not shown), to cover the exposed conduit and reservoir and prevent contamination. The protective layer is desirably translucent, so that accumulation of sample in the reservoir can be viewed by the user.

The conduit 26 terminates at and feeds into sample reservoir 29. The open end of conduit 26 is formed within the side wall of the reservoir 29. As shown in FIGS. 5 and 6, reservoir 29 is conically shaped, i.e., has a surface area that is increased relative to conduit 26, but thereafter decreases toward the sample deposition channel. At its top, reservoir 29 is open to the air. At its bottom, reservoir 29 opens into a channel extending laterally therefrom, which forms the linear sample deposition channel 28. As shown in FIGS. 5 and 6, the leading side wall 33 of the deposition channel is resected, so that carrier positioned thereunder abuts the longer trailing side wall 33' and thereby is registered directly under the opening of the channel, to receive sample therefrom. This beveling of the side walls forming the sample deposition channel further ensures that sample deposited from the channel is free to flow forward along carrier 22, and so that flow is resisted in the opposite direction.

By this design, sample received at port 18 is drawn by surface tension minimization, capillary action and gravity into conduit 26, flows therealong by capillary action and gravity into reservoir 29 which then fills and empties by gravity and capillary action into channel 28 which then fills by capillary action until sample meets carrier 22 and is drawn thereonto for movement by capillary flow into the detection channel and across the capture reagent line.

To encourage this type of flow, it will be appreciated that housing upper member 16 is suitably formed for any material that is wettable and can be machined or otherwise shaped to introduce the features of the present sample delivery system. Suitable such materials are in common use in the diagnostics industry and include hydrophilic plastics material, such as acrylic, including methacrylates and polymethacrylates. On the other hand, the housing base member desirably is formed of machinable, hydrophobic plastics material, to repel diffusion of sample onto the base member from the carrier. Suitable such materials include polystryrene.

As noted, the deposition channel 28 is formed as a linear channel having particular attributes that constitute valuable embodiments of the present invention. The length of channel 28 is greater than the width of detection channel 34. In this situation, the dynamics of sample flow are altered to encourage greater interaction between analyte and reagents at the entry to the detection channel, which elevates the concentration of labeled analyte entering the detection zone. In addition, the linear nature of the deposition channel, and of the sample band that is deposited therefrom onto the carrier, provides simple structure that can readily be machined into the upper housing and eliminates the need for any complicated curved or two dimensional structure.

Notwithstanding that the linear sample band is wider than the detection channel, it is now shown that very little sample stagnation occurs at the entry to the detection channel, and accordingly there is virtually no reduction in the volume of sample delivered across the analyte capture line. This is evident in FIG. 7, which is referenced in more detail in the Example herein.

It will be appreciated that a device having the present sample delivery features can be operated using a carrier that has features different from those herein described. For instance, and for simplicity, a device having the present sample delivery system can be operated using a carrier that is a single sheet of material. The single sheet of material can be simply rectangular in shape, and accommodated within a housing adapted to receive it. Alternatively, the single sheet of carrier material can be shaped as herein described, to provide a sample pad that is wider than the integral detection pad. This alternative carrier design can readily be accommodated by the housing described herein. It is a preferred embodiment of the present invention that the carrier consist of the array of pads hereindescribed.

Moreover, it will also be appreciated that the carrier pad array described herein can be used with a housing having a design that is quite different from that preferred herein. It is sufficient that any housing is provided simply with a means for depositing sample at a position upstream of the detector reagents deposited on the sample pad. In this respect, one can use the carrier pad array as such, and simply deposit sample by hand onto the sample pad. Alternatively, the carrier pad array can be housed within a device that deposits sample by any mechanism, including for instance by depositing the sample from a U-shaped sample deposition channel as described for instance in U.S. Pat. No. 6,171,870 and family.

In use, a user holds the present device in one hand with the top of the device facing the user or tilted somewhat toward the user. With the other hand, a drop or more of liquid sample is touched to the receiving port 18 and the device is then held in this position until sufficient sample is drawn into the device. Desirably, but not essentially, housing upper member 16 is made of material that allows the user to see that a coloured sample has migrated into and accumulated in the reservoir 29. The device is then laid flat on a work surface, and the results of the test can then either be viewed or determined instrumentally within about 5-20 minutes by detecting the presence of label at the detection line positioned within window 20.

It will be appreciated that the present device can be utilized to detect a wide variety of analytes present in numerous different sample types. These include environmental samples such as wastewater, and medical samples that include blood, its components, urine, cerebrospinal fluid, etc. In an embodiment of the present invention, the device is utilized to detect analytes present in whole blood. Such analytes include myoglobin, troponins including TnI, TnT, and TnC, myosin light chain, fatty acid binding protein, actin, CK-MB, CA-III, BNP,and the like, as well as markers of viral, bacterial, fungal and tumour burden, such as PSA, her-1 and her-2. In another embodiment, the device is utilized to detect urine-borne analytes, including hCG, LH, GnRH, drugs of use and abuse, markers of metabolism such as glucose, and the like. The reagents required to conduct assays for these analytes are all available commercially.

In addition, it will be appreciated that the present device can be adapted to detect more than one analyte in a single test. For this purpose, the carrier of the device will comprise mobile, labeled detector reagents for each analyte deposited on the sample pad, and immobilized capture reagents for the resulting analyte complexes, positioned as separate bands or other indicia on the detector pad in full view from window 20.

Use of a device of the present invention is now described in detail in the following examples.

EXAMPLES

The following results have been obtained by applying the illustrated device in a model system in which the carrier is comprised of the illustrated pad array, where the sample pad is wider than the detection zone formed by the detection pad and bridging pad (absent a wicking pad and without adhesive tape over the detection channel). In the model system, gold conjugated mouse antibody to CK-MB, a cardiac analyte, is used as the labeled detector reagent, which reveals the pattern of sample flow along the carrier. Immobilized goat antibody to CK-MM was used as capture.

More particularly, gold conjugated mouse anti-CKMB (Spectral Diagnostics, Toronto, Canada) solution ($OD_{530}$=40) was prepared by mixing one volume of Stabil-Guard (SurModics, Inc., Eden Prairie, Minn., USA) and one volume of mouse anti-CKMB gold conjugate ($OD_{530}$=80).

As sample pad, a polyester supported cellulose nitrate membrane (PuraBind, 3 µm nominal pore size; Whatman International Ltd., Maidstone, Kent, UK) was first blocked by immersion into a blocking solution (StabilCoat (SurModics, Calif., USA)/$H_2O$=1/3, v/v). After drying, gold conjugated mouse anti-CKMB antibody ($OD_{530}$=40) was deposited as 0.5 µl dots onto the blocked sample pad by manual pipetting and dried at 37° C. For the detection zone, a polyester supported cellulose nitrate membrane (PuraBind, 5 µm nominal pore size; Whatman International Ltd., Maidstone, Kent, UK) was first blocked by immersion into a blocking solution (StabilCoat (SurModics, Calif., USA)/ $H_2O$=1/3, v/v). After drying, capture line was streaked onto the detection pad using an IsoFlow™ Dispenser (Imagene Technology, Hanover, N.H., USA) with an antibody solution containing 2 mg/ml goat anti-CKMM (Spectral Diagnostics, Inc., Toronto, Canada), 1% sucrose, and 3% methanol.

The carrier was assembled by putting the sample pad and the detection pad with attached bridging pad in the restricted compartments in the base member of the device respectively so that the cellulose nitrate layers of the sample pad and the bridge are facing each other, and the liquid communication between these layers was secured by pressing the upper member of the device housing into the base member (FIG. 5).

Example 1

The converging pattern of sample flow toward the detection channel was first confirmed, in an experiment in which normal human serum was delivered as a linear band from the deposition channel and then permitted to flow for about ten minutes toward the detection channel. The bridge was then removed, thereby stopping sample flow within the sample pad, to reveal the label flow pattern. As illustrated in FIG. 7A, the labeled detector antibodies entrained within the migrating sample clearly displayed flow converging toward the bridging pad of the detection zone. This same converging sample flow is seen in assays that run to completion without bridging pad interruption. Notwithstanding the reduced width of the detection channel relative to the span of labeled detector antibody deposited on the sample pad, there was very little detectable stagnation of reagent or sample in the shoulders of the sample pad. Substantially all of the sample and reagent migrated toward the bridge leading into the detection channel. There is accordingly no need to shape sample deposition channels for confocal sample flow; a linear sample deposition band is sufficient to drive the desired flow into the detection channel.

Example 2

Figure 7B:
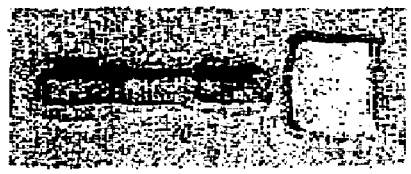
Figure 7C:
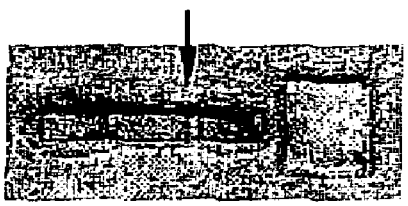
Figure 7D:
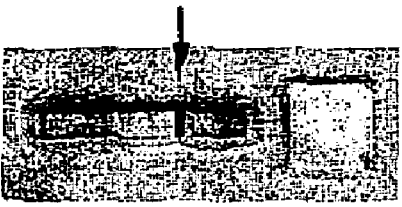

The carrier pad arrangement just described was also employed in the present device for the detection of rCKMB, as analyte. In this assay, 50 µl of normal human serum alone or spiked with rCKMB was tested. The results at 15 min are illustrated in FIGS. 7B (normal human serum), 7C (normal human serum spiked with 6.25 ng/ml rCKMB), and 7D (spiked with 32.35 ng/ml rCKMB). These Figures reveal that label deposited on the sample pad flowed almost completely out of the sample pad and into the detection zone, there being very marginal and negligible stagnation of labeled reagents in the sample pad shoulders. The results also reveal that rCKMB is detected in the spiked samples, the assay being more sensitive to detection of CKMB at the higher concentrations.

Example 3

Figure 7E:
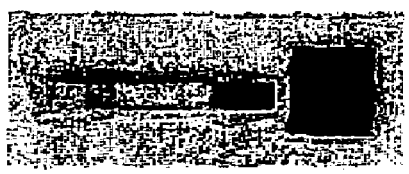

The device also was assessed for its ability to retard the flow of red blood cells, so that they do not migrate into and obscured results otherwise visible at the capture line. To this end, 50 µl of fresh heparinized human whole blood was tested. After 15 min, the majority of the red blood cells were retained in the sample pad, and the front of the red blood cells was restricted at the center of the bridging pad. After about 1 hour, the front of the red blood cells was stabilized at just beyond the bridge before reaching the capture line within the read-out window, and remained there afterwards. Hemolysis was not visually detectable. The result at 72 hours is shown in FIG. 7E. It will thus be appreciated that the bridging pad and its elevation relative to the sample and detection pads also contributes to the filtration of sample particulates including red blood cells, and that this carrier pad array is particularly well adapted for detection of soluble analytes present in blood samples.

While the invention has been exemplified with reference to a particular diagnostic assay and format, it will be appreciated that any of a variety of lateral flow type assays can be conducted to detect a variety of analytes present in different liquid

I claim:

1. A device of the type useful to perform a lateral flow immunodiagnostic assay for one or more target analytes, the device comprising:
   (a) a carrier for conducting the flow of sample along a path, the carrier comprising:
      a sample receiving zone comprising a detectably labeled, mobile detector reagent for binding to the target analyte, and
      an analyte detection zone downstream of the sample receiving zone and comprising an immobilized capture reagent for capturing a complex formed by said analyte and said detector reagent, and
   (b) a housing for receiving the carrier, the housing comprising
      a sample receiving system and
      a sample deposition system in flow communication with the sample receiving system and the carrier, wherein the sample deposition system delivers sample from the sample receiving system onto the carrier as a sample band that is essentially linear and has a width greater than the width of the analyte detection zone, the width being transverse to the path of sample flow.

2. The device according to claim 1, wherein the sample receiving zone and the analyte detection zone are defined on distinct carrier pads having an upper surface and a lower surface, and wherein said pads are coupled for sample flow by a bridging pad.

3. The device according to claim 2, wherein the bridging pad and the analyte detection zone pad are held in flow communication with one another through a wettable barrier layer that contacts both the bridging pad and the analyte detection zone pad.

4. The device according to claim 3, wherein the bridging pad has a width narrower than the length of the sample band deposited from the sample deposition system.

5. The device according to claim 3, wherein the sample deposition system comprises
 a sample inlet system and
 a sample deposition channel in communication with the sample inlet system to deliver sample to a sample deposition site on the carrier.

6. The device according to claim 5, wherein the sample deposition channel is integrated within the housing.

7. The device according to claim 1, wherein the detectably labeled, mobile detector reagent is labeled with a tag selected from gold sol, enzyme, fluorophore, or lumiphore.

8. The device according to claim 1, wherein the analyte detection zone further comprises an immobilized binding partner that is specific for the detector reagent and non-specific for the analyte.

9. The device according to claim 2, wherein the bridging pad has a lower surface in contact with at least a portion of the sample receiving zone pad and at least a portion of the analyte detection zone pad.

10. The device according to claim 2, wherein the sample receiving zone pad comprises a porous material.

11. The device according to claim 2, wherein the analyte detection zone pad comprises a porous material.

12. The device according to claim 2, wherein the bridging pad comprises a porous material.

13. The device according to claim 3, wherein the wettable barrier layer is water-impermeable and comprises a translucent or transparent material.

14. The device according to claim 5, wherein the sample inlet system comprises:
 a sample reservoir in communication with the sample deposition channel; and
 a conduit in communication with the sample inlet system and the sample reservoir to conduct sample flow.

15. The device according to claim 14, wherein the conduit is reticulated.

16. The device according to claim 5, wherein the length of the sample deposition channel is greater than the width of the analyte detection zone.

* * * * *

UNITED STATES PATENT AND TRADEMARK OFFICE
CERTIFICATE OF CORRECTION

PATENT NO.        : 7,256,053 B2  
APPLICATION NO. : 10/279566  
DATED              : August 14, 2007  
INVENTOR(S)      : Wei Hu Page 1 of 1

It is certified that error appears in the above-identified patent and that said Letters Patent is hereby corrected as shown below:

At Col. 10, line 41, after "different liquid" add -- samples. --.

Signed and Sealed this

Twenty-third Day of October, 2007

JON W. DUDAS  
*Director of the United States Patent and Trademark Office*